(12) United States Patent
Ünlü et al.

(10) Patent No.: US 10,488,328 B2
(45) Date of Patent: Nov. 26, 2019

(54) POLARIZATION ENHANCED INTERFEROMETRIC IMAGING

(71) Applicant: TRUSTEES OF BOSTON UNIVERSITY, Boston, MA (US)

(72) Inventors: M. Selim Ünlü, Newton Highlands, MA (US); George Daaboul, Amesbury, MA (US); Abdulkadir Yurt, Brighton, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 15/123,763

(22) PCT Filed: Mar. 6, 2015

(86) PCT No.: PCT/US2015/019136
§ 371 (c)(1),
(2) Date: Sep. 6, 2016

(87) PCT Pub. No.: WO2015/134847
PCT Pub. Date: Sep. 11, 2015

(65) Prior Publication Data
US 2017/0016821 A1 Jan. 19, 2017

Related U.S. Application Data

(60) Provisional application No. 61/949,803, filed on Mar. 7, 2014.

(51) Int. Cl.
*G01N 21/21* (2006.01)
*G01N 21/45* (2006.01)
(Continued)

(52) U.S. Cl.
CPC ......... *G01N 21/21* (2013.01); *G01B 9/02011* (2013.01); *G01N 21/45* (2013.01);
(Continued)

(58) Field of Classification Search
CPC ......... G01B 2290/70; G01J 2009/0261; G01N 21/21; G01N 2021/216
See application file for complete search history.

(56) References Cited

U.S. PATENT DOCUMENTS 4,869,593 A 9/1989 Biegen
5,235,404 A * 8/1993 Fejer .................... G02B 21/002
356/460

(Continued)

FOREIGN PATENT DOCUMENTS

WO 2011/014282 A1 2/2011
WO 03/067229 A1 8/2013

OTHER PUBLICATIONS

Ha, Thesis: Absorption and Scattering of Single Plasmonic Nanoparticles:, Rice University, 2010, 83 pp.
(Continued)

*Primary Examiner* — Michael P LaPage
(74) *Attorney, Agent, or Firm* — Nixon Peabody LLP; Ronald I. Eisenstein; David F. Crosby

(57) ABSTRACT

An imaging system uses polarized light to illuminate the target and then uses a polarization filter to remove the light that is reflected from the target without modification. The target can include one or more anisotropic objects that scatter the light and alter the polarization state of the reflected light and causing it to be selectively transmitted to the imaging device which can record the transmitted light through the filter. The illuminating light can be circularly polarized and the filter can remove the circularly polarized light. The target can include asymmetric nanoparticles, such as nanorods that alter the amplitude or phase of the scattered light enabling pass through the filter to be detected by the imaging device.

21 Claims, 12 Drawing Sheets

(51) Int. Cl.
  *G01B 9/02* (2006.01)
  *G01N 21/552* (2014.01)
(52) U.S. Cl.
  CPC ..... *G01N 21/554* (2013.01); *G01N 2021/216* (2013.01); *G01N 2201/0683* (2013.01); *G01N 2201/06113* (2013.01)

(56) References Cited

U.S. PATENT DOCUMENTS

| | | | | |
|---|---|---|---|---|
| 6,219,139 | B1* | 4/2001 | Lesniak | G01L 1/241 |
| | | | | 356/34 |
| 8,003,316 | B2 | 8/2011 | Frasch et al. | |
| 2004/0252301 | A1* | 12/2004 | Kawano | G01N 21/45 |
| | | | | 356/369 |
| 2005/0264813 | A1* | 12/2005 | Giakos | B82Y 20/00 |
| | | | | 356/369 |
| 2008/0002212 | A1* | 1/2008 | Kawasaki | G01B 9/02019 |
| | | | | 356/512 |
| 2010/0020168 | A1* | 1/2010 | Ye | G01N 21/21 |
| | | | | 348/92 |
| 2010/0118293 | A1* | 5/2010 | Wu | G01N 21/21 |
| | | | | 356/33 |
| 2011/0276166 | A1* | 11/2011 | Atanasoff | G01B 11/0625 |
| | | | | 700/104 |
| 2012/0213704 | A1 | 8/2012 | Awdeh et al. | |
| 2012/0238471 | A1 | 9/2012 | Pinchuk | |
| 2013/0100333 | A1* | 4/2013 | Awatsuji | G03H 1/0443 |
| | | | | 348/335 |
| 2014/0322547 | A1* | 10/2014 | Petzold | A01N 55/00 |
| | | | | 428/429 |

OTHER PUBLICATIONS

Li et al., "Polarization-sensitive reflectance imaging in skeletal muscle", Opt Express, 16(13):9927-35 (2008).
Daaboul et al., "Label-Free Optical Biosensors for Virus Detection and Characterization", IEEE Journal of Selected Topics in Quantum Electronics 18(4):1422-1433 (2012).
Daaboul et al., "High-Throughput Detection and Sizing of Individual Low-Index Nanoparticles and Viruses for Pathogen Identification", American Chemical Society, doi 10.1021 (2010).
Daaboul et al., "LED-based Interderometric Reflectance Imaging Sensor for quantitative dynamic monitoring of biomolecular interactions", Bioelectron, doi:10.1016 (2010).
Hong et al., "Background-Free Detection of Single 5 nm Nanoparticles through Interferometric Cross-Polarization Microscopy", American Chemical Society, 11: 541-547 (2011).
Lopez et al., "Label-free, multiplexed virus detection using spectral reflectance imaging", Bioelectron (2011).
Yurt et al., "Single nanoparticle detectors for biological applications", Nanoscale 4(3) 715-726 (2012).

* cited by examiner

Optical Setup 1

POLARIZATION ENHANCED INTERFEROMETRIC IMAGING

CROSS-REFERENCE TO RELATED APPLICATIONS

This application claims benefit under 35 U.S.C. § 119(e) of the U.S. Provisional Application No. 61/949,803, filed Mar. 7, 2014, the contents of which are incorporated herein by reference in their entirety.

STATEMENT REGARDING FEDERALLY SPONSORED RESEARCH

This invention was made with Government Support under Contract No. EB015408 awarded by the National Institutes of Health. The Government has certain rights in the invention.

CROSS-REFERENCE TO RELATED APPLICATIONS

This application is a 35 U.S.C. § 371 National Phase Entry Application of International Application No. PCT/US2015/019136 filed Mar. 6, 2015, which designates the U.S., and which claims benefit under 35 U.S.C. § 119(e) of the U.S. Provisional Application No. 61/949,803, filed Mar. 7, 2014, the contents of each of which are incorporated herein by reference in their entireties.

REFERENCE TO MICROFICHE APPENDIX

Not Applicable

BACKGROUND

Technical Field of the Invention

The present invention is directed to methods and systems interferometric detection of nanoparticles.

Description of the Prior Art

The ability to rapidly detect small particles, such as, biological target molecules including DNA, RNA, and proteins, as well as nanomolecular particles such as virions, is fundamental to our understanding of both cell physiology and disease progression, as well as for use in various applications such as early and rapid detection of disease outbreaks and bioterrorism attacks. In some systems, the detection is limited by the need to use labels, such as fluorescent molecules or radiolabels, which can alter the properties of the biological target, e.g., conformation, and which require additional, often time-consuming, steps. Other systems have been developed by the some of the present inventors that obviate the need for such labels.

For example, U.S. Pat. No. 7,695,680 discloses a Resonant Cavity Biosensor that provides a high throughput detection system without the use of labels. The disclosure of U.S. Pat. No. 7,695,680 is hereby incorporated by reference in its entirety.

Another example is PCT/US2006/015566 which discloses the use of a layered substrate for use in a label free detection system. The disclosure of PCT/US2006/015566 is hereby incorporated by reference in its entirety.

A further example is PCT/US2011/033397 which discloses a spectral reflectance imaging system that uses multiple discrete light sources in a label free detection system. The disclosure of PCT/US2011/033397 is hereby incorporated by reference in its entirety.

SUMMARY

Methods and systems according to the present invention enable the detection of very small nanoparticles and can be used, for example, in biomarker discovery and diagnostics. The present invention can be used in research enabling scientists to monitor molecular interactions at the molecular level.

For biomarker discovery and diagnostics, methods and systems according to the invention can enable up to 1000× higher sensitivity than fluorescence without increasing cost. The invention allows for screening in complex biological media like whole blood without the need for costly sample preparation. Another advantage of the invention is that it enables researchers to make measurements under native physiologically relevant conditions.

The present invention can be used to improve the sensitivity and performance of existing imaging systems, such as an Interferometric Reflectance Imaging Sensor (IRIS) imaging system. The IRIS imaging system includes a light source directed at a substrate having a first reflective surface and transparent layer forming a second reflective surface spaced apart from the first reflective surface. The light reflecting from the two surfaces produces an interference signal that is modified by particles on the surface and can be used to detect nanoparticles on the surface of the transparent layer. The nanoparticles can include binding sites for detecting molecules such as proteins.

In accordance with some embodiments of the invention, the method includes focusing circularly polarized light at a target and collecting the reflected, scattered and/or transmitted light. The collected light can be passed through a filter and an image of the light can be recorded by an imaging device, such as a CCD sensor in a camera.

In accordance with some embodiments of the invention, the system includes a light source adapted to direct circularly polarized light at a target, such as substrate, an analyzer the receives light that is either reflected from the target, transmitted through the target or scattered by the target, and an imaging device, such as a CCD sensor that records the light that is filtered by the analyzer. The analyzer can be configured to filter circularly polarized light that is directly reflected by the target. However, where the surface of the target includes one or more nanoparticles or molecules bound to the surface, the transmission, scattering and reflection by these elements will modify the polarization state of the light and enable the light to pass through the analyzer to be captured by the imaging device. Where the nanoparticles are anisotropic, such as nanorods, the size and orientation of these nanoparticles can be used as labels to differentiate the nanoparticles and their binding sites.

In accordance with implementations of the invention, one or more of the following capabilities can be provided. The present invention provides a low cost imaging system that can detect single molecules. The present invention provides a low cost imaging system that can detect single molecules using a lower magnification and smaller numerical aperture. The present invention provides a low cost imaging system that can detect single molecules using a lower magnification and smaller numerical aperture, thus providing a larger field of view and enabling higher throughput scanning.

These and other capabilities of the invention, along with the invention itself, will be more fully understood after a review of the following figures, detailed description, and claims.

BRIEF DESCRIPTION OF THE FIGURES

The accompanying drawings, which are incorporated into this specification, illustrate one or more exemplary embodiments of the inventions and, together with the detailed description, serve to explain the principles and applications of these inventions. The drawings and detailed description are illustrative, and are intended to facilitate an understanding of the inventions and their application without limiting the scope of the invention. The illustrative embodiments can be modified and adapted without departing from the spirit and scope of the inventions.

This application file contains at least one drawing executed in color. Copies of this patent application publication with color drawing(s) will be provided by the Office upon request and payment of the necessary fee.

FIG. 4A also shows the signal to noise ratio of a signal from an imaging system according to the invention that uses less than half the magnification.

FIG. 4A shows an image of a substrate that includes single molecule detectors

DETAILED DESCRIPTION OF PREFERRED EMBODIMENTS

The present invention is directed to methods and systems for detecting and producing images of nanoparticles. These systems and methods can be used to provide low cost, high throughput imaging systems for detecting small particles including microparticles and nanoparticles, such as biomarkers, and single molecules such as proteins and RNA/DNA. The methods and systems according to the present invention can be used to improve the performance of existing imaging systems without increasing the cost.

In accordance with some embodiments of the invention, imaging can be improved by reducing the specular (reference) light that is received from the target substrate. In accordance with some embodiments of the invention, the substrate can be illuminated with polarized light and the light received from (or through) the substrate can be processed through an analyzer that blocks the specular (reflected/transmitted) reference light allowing only light that interacted with an anisotropic object to be captured by the camera.

In accordance with some embodiments of the invention, the substrate can be illuminated by circularly polarized light and the light received from the substrate can be processed to filter the circularly polarized light, leaving only light that was modified by interaction with target particles and molecules.

Figure 1:
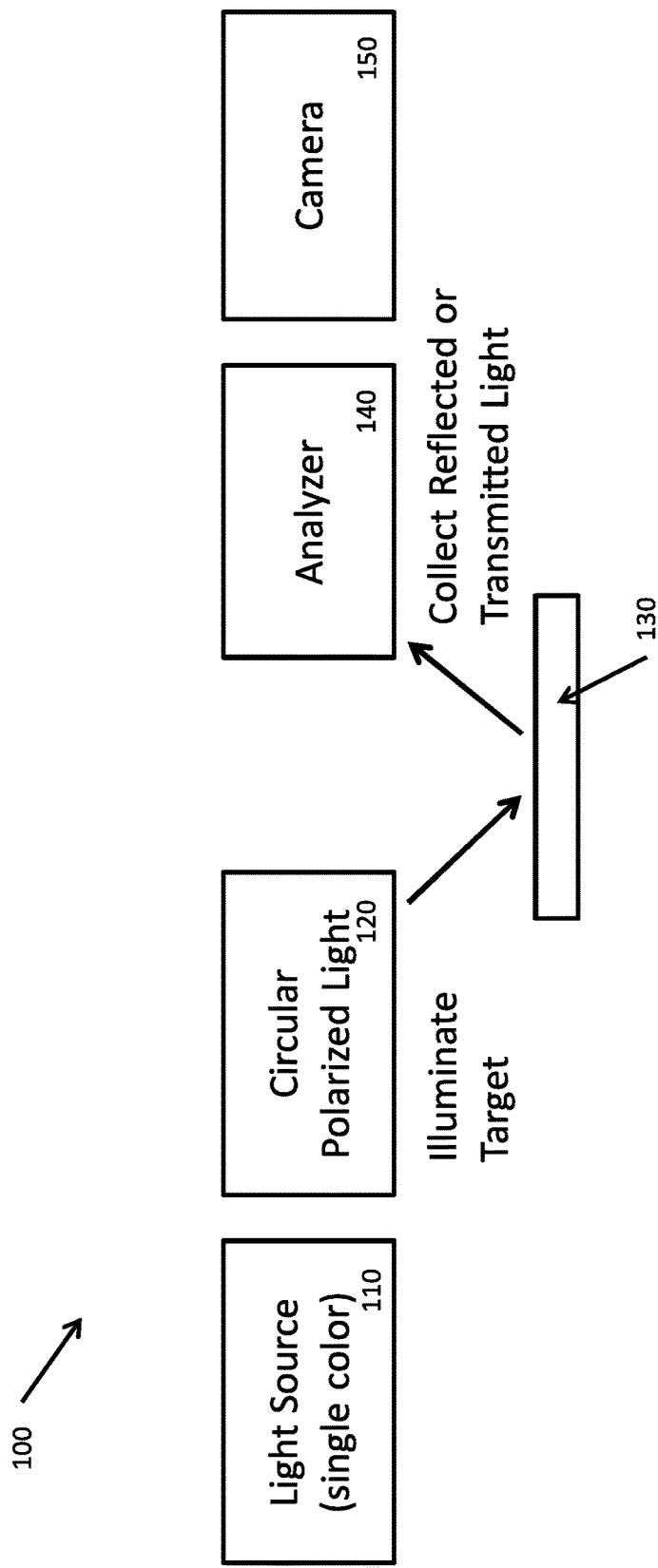
FIG. 1 is a block diagram of an imaging system according to the invention.

FIG. 1 shows a diagrammatic view of imaging system according to the present invention. In accordance with some embodiments of the invention, a light source 110 can be used to direct light along an illumination path that includes one or more light processing elements 120 that produce circularly polarized light that can be used to illuminate a target 130. The light source 110 can include, for example, one or more light emitting diodes (LEDs) or a superluminsecent diodes (SLDs) or a broad band light source and a filter. In accordance with some embodiments of the invention, the bandwidth of the light can be <200 nm, <100 nm, <50 nm or <30 nm. The light processing elements 120 can include, for example, a linear polarizer and a quarter wave plate (oriented at the proper angle, e.g. 45 degrees) which can be used to produce circularly polarized light on the illumination path toward the target. The target 130 can be, for example, a nanoparticle attached to a substrate. The target substrate can be configured to reflect light, scatter light and/or transmit the illuminating light.

Upon reflection, transmission or scattering from an isotropic target (objects or bare flat surfaces), the circular nature of the polarization will be preserved (although the handedness is flipped if it is in reflection mode). However, the reflecting and/or scattering from anisotropic objects such as a nanorod particles or a wedge alters the polarization state of the light by modifying the amplitude or phase of the reflected or scattered light in one axis. Thus, for example, the anisotropy in the interaction between the light and the particle will break the symmetry in the circularly polarized light and form an elliptically polarized light in the far-field.

The reflected, scattered and/or transmitted light travels along a collection path to an imaging device that includes an imaging sensor (e.g., a camera) that can detect and record the reflected, scattered and/or transmitted light. An optical filter 140, for example, consisting of a quarter waveplate and an analyzer in the collection path can be configured to transmit any polarization state but circularly polarized light. The quarter waveplate in the filter 140 can be used to convert the circularly polarized light into linearly polarized light and then the analyzer (e.g., linear polarizer) oriented orthogonal to the polarization of the light processing elements 120 can be used to selectively filter the unmodified light completely. Any anisotropy in the polarization state of the light will lead to imperfect filtering and thus will be transmitted to the imaging device 150 (e.g., CCD camera). Therefore the light not interacting with the objects or perfectly isotropic objects will be blocked whereas the light interacting with the anisotropic object can be selectively transmitted.

In accordance with some embodiments of the invention, optical enhancement can be further increased by combining circularly polarized light illumination with metallic nanorods that have a large scattering or absorption cross section between the short and long axis of the nanorod. For example, in some embodiments, gold nanorods having a high aspect ratio (e.g., 10 nm by 60 nm) can be used. In accordance with some embodiments, the long axis of the gold nanorod can have a plasmonic resonance at a wavelength that overlaps with the illumination wavelength. In this embodiment, the nanorod does not need to have a large aspect ratio but one of the axes has to be in resonance with the frequency of the illuminating light. In accordance with some embodiments, different illumination frequencies can be used to illuminate one or more nanorods from a set of different size nanorods, each having a known plasmonic resonance. The optimization of the resonant or non-resonant system can be done using numerical methods such as finite-difference-time-domain (FDTD), finite-element (FE) methods, or analytical or semi-analytical methods based on Green's Function or Mie Theories. These methods can be used to estimate the far-field polarization properties of anisotropic objects such as nanorods, nanospheres, nanocubes etc. and electro-magnetically coupled nanoparticles in general.

In accordance with some embodiments of the invention, the illumination path and the collection can be aligned such that some or all of the components of the light processing elements 120 can also be part of the optical filter 140.

The present invention can be applied to any imaging system that can be modified to include polarized light in the illumination path and a filter in the collection path.

Figure 2:
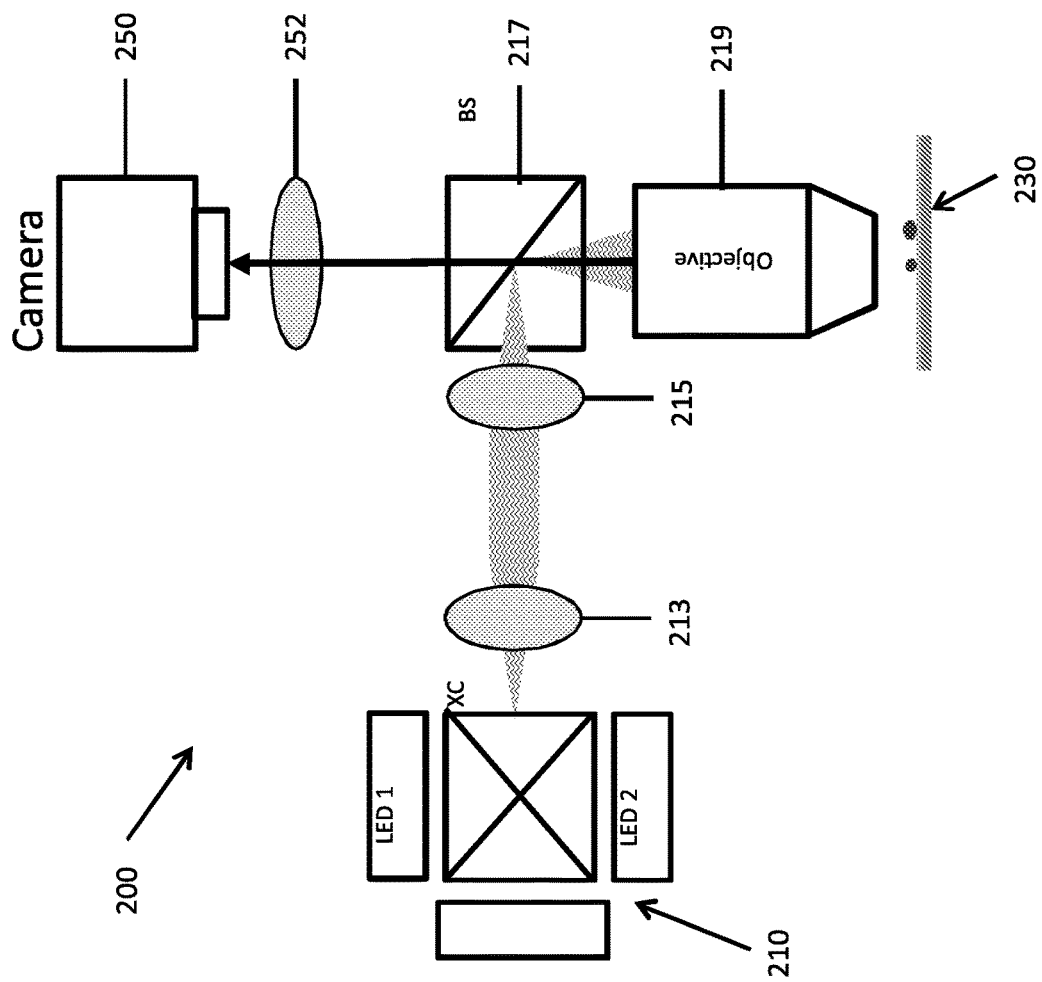
FIG. 2 is a block diagram of an IRIS imaging system according to the prior art.

For example, the Interferometric Reflectance Imaging Sensor (IRIS) is a low-cost, compact and simple to use biosensing platform that can be modified according to embodiments of the present invention. FIG. 2 shows a diagrammatic view of an IRIS imaging system. The IRIS imaging system 200 can include an LED light source 210 for illuminating a target substrate 230. The illumination path can include focusing lenses 213 and 215, a beam splitter 217 and an objective lens 219 that directs and focuses the light on the target 230. The collection path can include the objective lens 219, the beam splitter 217 and a focusing lens 252 that directs and focuses the light reflected from target 230 on the imaging sensor of the camera 250.

IRIS has demonstrated high-throughput detection and quantification of protein-protein binding, DNA-protein binding and DNA-DNA hybridization in real-time with high sensitivity and reproducibility. Recent advancements have enabled the IRIS technology to identify individual captured nanoparticles based on size and shape. This new modality of IRIS is termed single-particle IRIS (SP-IRIS). SP-IRIS shines light from an LED source on nanoparticles bound to a substrate surface, which consists of an oxide layer (e.g., silicon dioxide) on top of a silicon substrate. The silicon substrate and the oxide layer reflect the light according to an interference pattern that is disturbed by the nanoparticles and molecules on the surface of the substrate.

Figure 3:
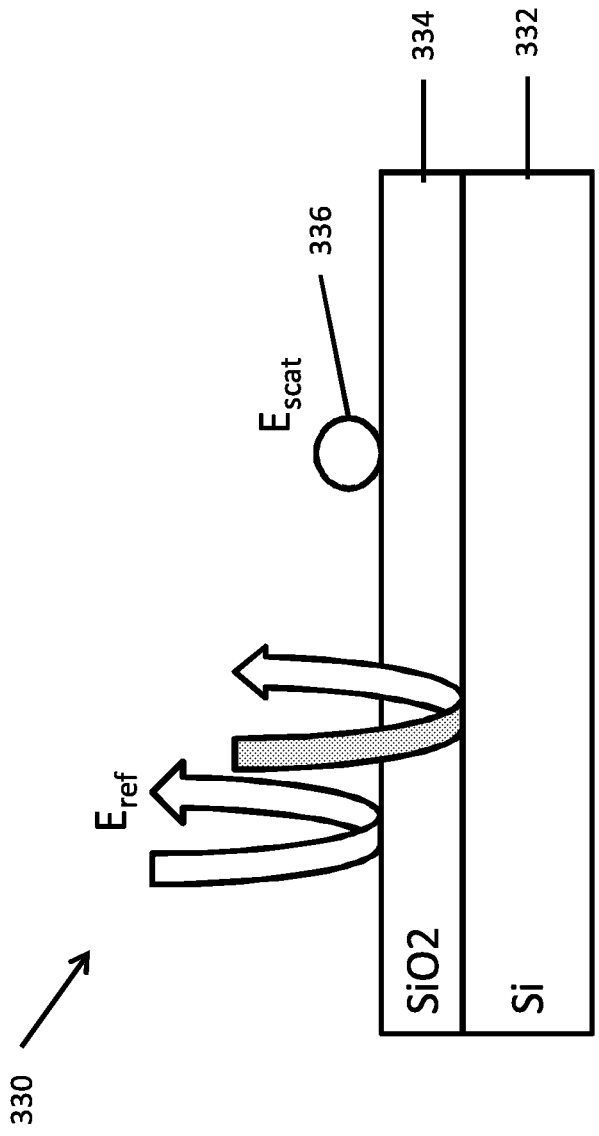
FIG. 3 is a diagrammatic view of a target substrate according to the invention.

FIG. 3 shows a diagrammatic view of a target 330 according to some embodiments of the invention. The target 330 can include a substrate that includes a silicon base layer 332 and an oxide layer 334 (e.g., silicon oxide). Using this target 330 configuration, the light traveling (e.g., $E_{ref}$) along the illumination path can be reflected by surface at the interface of the silicon base layer 332 and the oxide layer 334 and by top of the oxide layer 334. This can result in signal interference depending on the light wavelength and the thickness of the oxide layer 334. Where the target 330 includes a particle 336, the light is scattered (e.g., $E_{scat}$) and the interference of light reflected from the substrate surface is modified by the presence of particles producing a distinct signal that can be captured by a CCD camera 350. This appears as a dot on the image, and the size of the particle can be calculated using a forward model. Size discrimination reduces the noise from particles non-specifically bound. In an SP-IRIS image, as many as a million distinct nanoparticles can be simultaneously detected. SP-IRIS relies on efficient collection of scattered light from nanoparticles and thus requires high magnification (50×) and numerical aperture (0.8), which limits the field of view to less than 0.3 mm×0.3 mm using conventional CCD cameras. For DNA arrays with a 100 µm pitch, as many as about 10 spots can be imaged at once. To interrogate larger arrays, consecutive images can be taken to cover the entire IRIS sensor substrate. The use of functionalized gold nanoparticles as detection probes is sensitive and quantitative, allowing for single molecule counting.

In some embodiments of the aspects described herein, the target substrate 330 can be a layered substrate. In some embodiments, the layered substrate comprises 100-1000 nm of $SiO_2$ layered on a Si wafer. In some embodiments, the layered substrate comprises at least 100 nm of $SiO_2$ layered on a Si wafer. In some embodiments, the layered substrate comprises at least 200 nm of $SiO_2$ layered on a Si wafer. In some embodiments, the layered substrate comprises at least 300 nm of $SiO_2$ layered on a Si wafer. In some embodiments, the layered substrate comprises at least 400 nm of $SiO_2$ layered on a Si wafer. In some embodiments, the layered substrate comprises at least 500 nm of $SiO_2$ layered on a Si wafer. In some embodiments, the layered substrate comprises at least 600 nm of $SiO_2$ layered on a Si wafer. In some embodiments, the layered substrate comprises at least 700 nm of $SiO_2$ layered on a Si wafer. In some embodiments, the layered substrate comprises at least 800 nm of $SiO_2$ layered on a Si wafer. In some embodiments, the layered substrate comprises at least 900 nm of $SiO_2$ layered on a Si wafer. In some embodiments, the layered substrate comprises at least 1000 nm of $SiO_2$ layered on a Si wafer.

In accordance with some embodiments of the invention, the interferometric signal from the particle can be optimized by changing the thickness of the oxide layer that it sits on. Changing of the oxide layer thickness can be used to modulate the strength of the reflected field (e.g., $E_{ref}$) and the phase. These two variables are coupled due to the electromagnetic laws of interference.

In accordance with some embodiments of the invention, the intensity of the reference field (e.g., $E_{ref}$) in collection path can be modulated by providing a linear polarizer in the illumination path and a linear polarizer in the collection path of the optical setup and changing the angles between the polarizers to modulate the intensity of the (reflected) reference field (e.g., Eref) received by the imaging device.

When using circularly polarized light and an analyzer, as described herein, the polarization angle of the linear polarizer on the analyzer side (e.g., the collection path) can be adjusted with respect to the linear polarizer in the illumination path to optimize the reflected light intensity received by the imaging device.

Figure 4B:
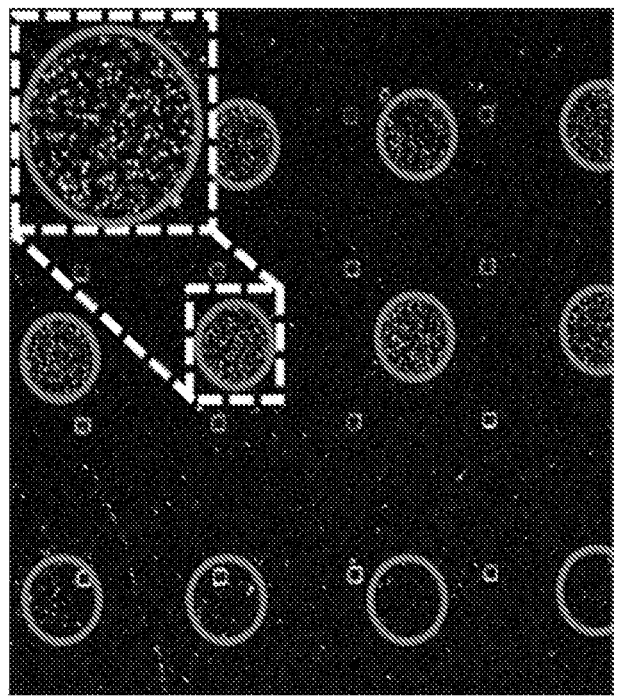
FIG. 4A shows a diagram comparing the signal to noise ratio of a signal from an imaging system that uses non-polarized light with a signal from an imaging system that uses circular polarized light according to the invention.
Figure 4A:
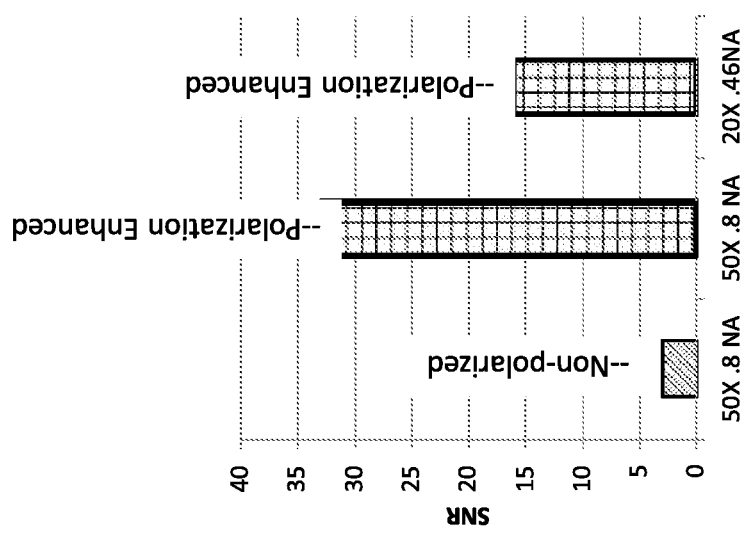

The SP-IRIS requires high magnification and numerical aperture (e.g., a 50 objective with 0.8 NA) to produce a sufficiently high signal to noise ratio to detect nanoparticle tags of approximately 40 nm. In accordance with some embodiments of the invention, the use of polarized illumination and filtering can provide improved signal to noise ratios and reduce the need to for high magnification and numerical aperature objective lenses, which can reduce the cost and improve the throughput of the system (e.g., provide a wider field of view). FIG. 4A shows the improvement of the signal to noise ratio of the SP-IRIS system when using polarization as compared the non-polarized SP-IRIS system. The graph shows that polarization provides significant improvement in signal to noise ratio when using a 20× magnification and 0.46 numerical aperture objective lens as compared to a non-polarized system using a 50× magnification and 0.8 numerical aperture objective lens. FIG. 4b shows a sample image showing single molecule counting using polarized illumination of gold nanorods that allows multiplexed detection of molecules without image scanning. Thus, as shown in FIG. 4B, imaging systems according to the present invention can have a wider field of view and enable increased throughput by providing single molecule resolution over a larger target area.

Figure 5A:
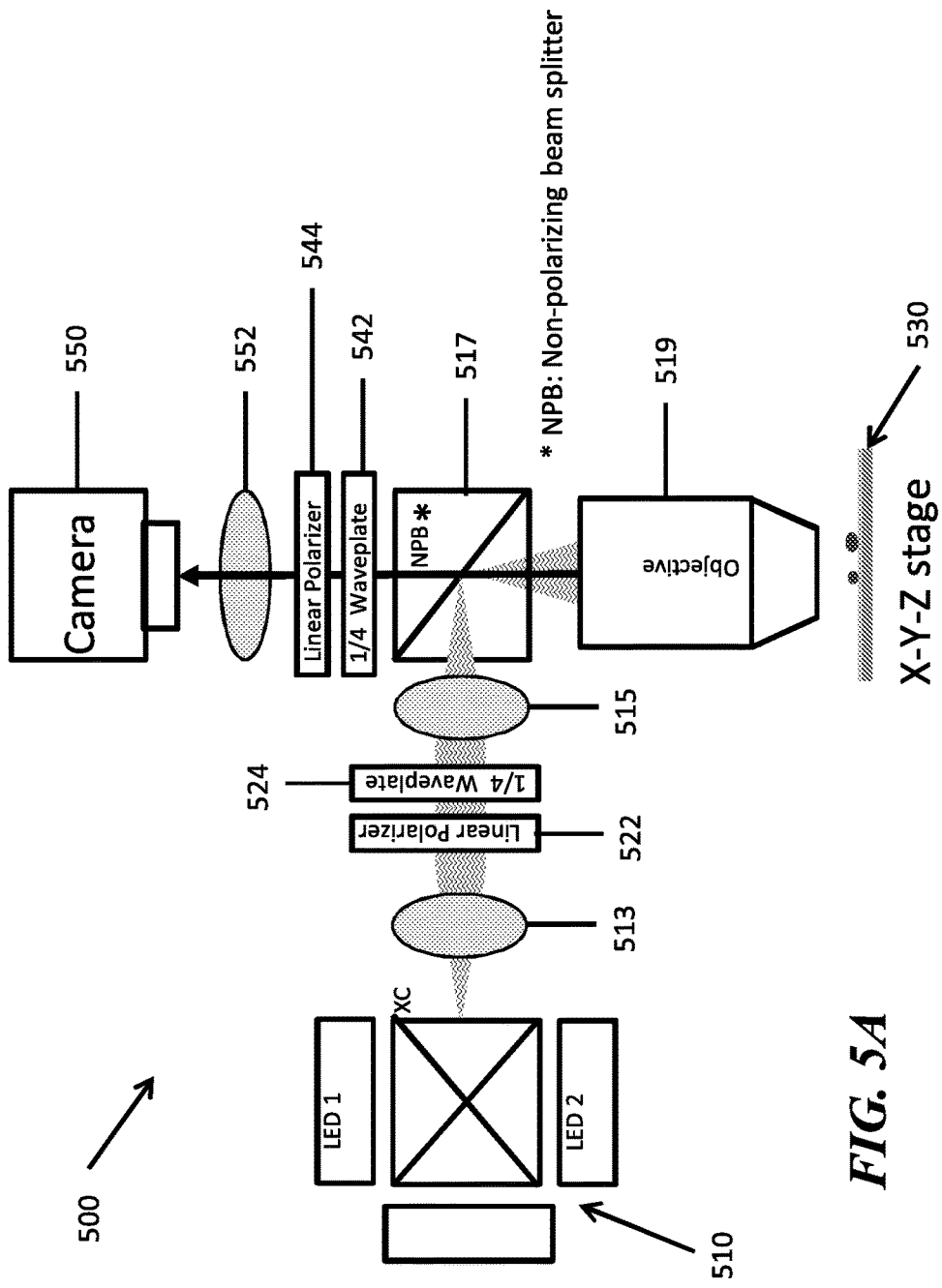
FIG. 5A shows a diagram of an imaging system according to one embodiment of the invention.
Figure 5C:
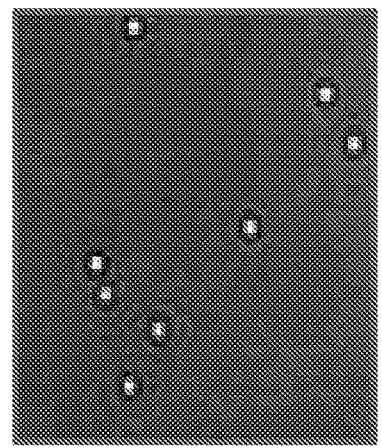
FIG. 5C shows an image of a substrate that includes single molecule detectors according to FIG. 5B.
Figure 5B:
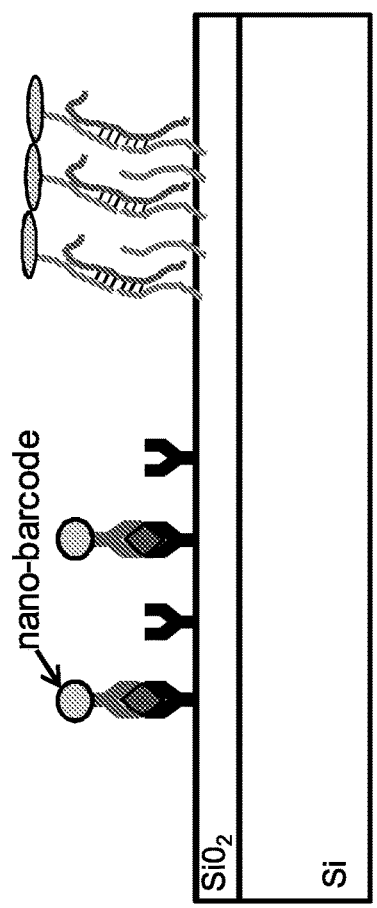
FIG. 5B shows a diagram of a target substrate that includes single molecule detectors with biomarkers.

FIGS. 5A, 5B, and 5C show an imaging system according to some embodiments of the present invention. FIG. 5A shows an SP-IRIS imaging system 500 that has been modified to provide polarization enhanced imaging. Imaging system 500 can include an LED light source 510 for illuminating a target substrate 530. The illumination path can include focusing lenses 513 and 515, a non-polarizing beam splitter 517 and objective lens 519 that directs and focuses the polarized light on the target 530. The collection path can include objective lens 519 and focusing lens 552 that focuses the light reflected from the target 530 on the sensor of the camera 550. The illumination path can also include a linear polarizer 522 and a quarter waveplate 524 that produces circularly polarized light. The target 530 can be mounted on an X, Y, and Z stage that enables the target to be positioned for imaging and focusing.

The collection path can include the objective lens 519, the beam splitter 517, a focusing lens 552 and an imaging device 550, such as a CCD camera. The collection path can also include a quarter wave plate 542 and a linear polarizer 544 to filter the reflected light from the target 350. In accordance with some embodiments, the linear polarizer 522 and the linear polarizer 544 can be arranged in an orthogonal configuration. In accordance with some embodiments of the invention, the objective 519 can have lower magnification (e.g., 5×, 10×, 15×, 20×, 25×, or 30×) and a smaller numerical aperture (e.g., in a range from 0.3-0.6 NA) than prior IRIS imaging systems.

In operation, the stage and the camera can be connected to a computer system that moves the target 130 in the X, Y and Z directions to produce images and video of the target that can be recorded by the computer system. The computer system can include one or more processors and associated memories that store computer programs (e.g., sets of instructions) that control the operation of the computer system and the imaging system. The computer system can also include computer programs that process the images and/or video to detect the presence of molecules, for example, as part of an assay. The computer program can process the images to identify high contrast areas that correspond to detected particles.

While FIG. 5A shows the light source to be one or more LEDs, in other embodiments of the invention, the light source can include a broadband light source and a or more filters that limit the bandwidth of the illumination to less than 100 nm and preferably less than 30 nm. In accordance with some embodiments the light source can include one or more LASERs.

FIG. 5B shows an example of a target 530 according to some embodiments of the invention. In these embodiments, the target 530 can include a substrate having a silicon layer and an oxide layer with binding sites on the oxide layer. Single molecules, such as proteins and DNA/RNA can become bound to the surface of the substrate and nanobarcode based tags can be selectively bound to the detected molecules to facilitate and confirm detection of target molecules. In prior systems, the barcodes that attached to the molecules to provide an optical signal for detection needed to be significantly larger than the molecule to enable visualization. One disadvantage of these large labels is that they can alter the properties of the detected molecules and inhibit or impact the effectiveness or efficiency of molecular interactions. One advantage of the present invention is that smaller and more efficient labels can be used to avoid the disadvantages of using larger labels.

FIG. 5C shows an example of an image produced by a system according to the invention. The image in FIG. 5C shows an image from a detection system that uses smaller and more efficient labels that is enhanced by filtering the background and enhancing the anisotropic optical response of the nanorods according to the invention. FIG. 5C shows a 600 μm×600 μm field of view sample image acquired using 4 Mp camera with 20×0.46 NA objective using polarization to improve the signal to noise ratio. The sample image uses nanorods to facilitate single molecule counting in a large field of view allowing multiplexed detection without the need of image scanning. Through further optimization the field of view can be increased to over 1 mm×1 mm allowing single molecule resolution over an array of at least 100 spots. Further optimization can be achieved by using an imaging device having a sensor with a larger area. Alternatively, a sensor with a smaller pixel size can allow the use of lower objective lens magnification while maintaining the same resolution. Additional optimization can be obtained by using a lower magnification objective lens having a higher numerical aperture.

Figure 6A:
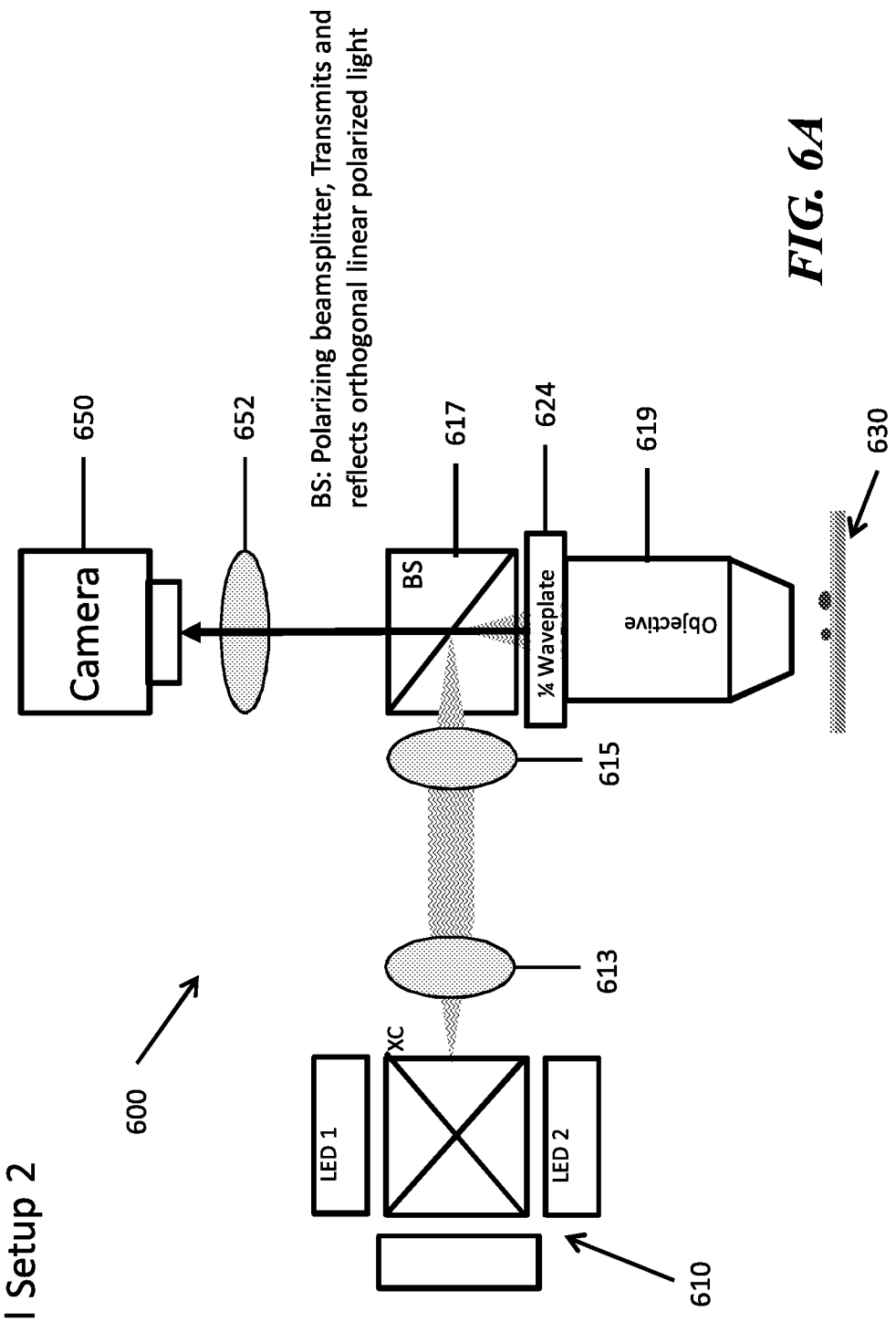
FIG. 6A shows a diagram of an imaging system according to an alternate embodiment of the invention.

FIG. 6A shows an IRIS polarization sensitive imaging system 600 according to some embodiments of the invention. Imaging system 600 can include an LED light source 610 for illuminating a target substrate 630. The illumination path can include focusing lenses 613 and 615, a polarizing beam splitter 617, a quarter waveplate 622, and an objective lens 619 that directs and focuses the polarized light on the target 630. The collection path can include objective lens 619 and focusing lens 652 that focuses the light reflected from target 630 on the sensor of the imaging device 650 (e.g., a CCD camera). The illumination path can also include a polarizing beam splitter 617 that transmits and reflects orthogonal linearly polarized light and a quarter waveplate 624 that produces circularly polarized light. The target 630 can be mounted on an X, Y, and Z stage that enables the target 630 to be positioned for imaging and focusing.

The collection path includes the objective lens 619, the quarter waveplate 622, the polarizing beam splitter 617, the focusing lens 652 and the imaging device 650. The collection path reuses the quarter wave plate 622 and a linear polarizer in the beam splitter 617 to filter the reflected circularly polarized light from the target 630. In accordance with some embodiments of the invention, the objective 619 can have lower magnification (e.g., 5×, 10×, 15×, 20×, 25×, or 30×) and a smaller numerical aperture (e.g., in a range from 0.3-0.6 NA) than prior IRIS imaging systems.

Figure 6B:
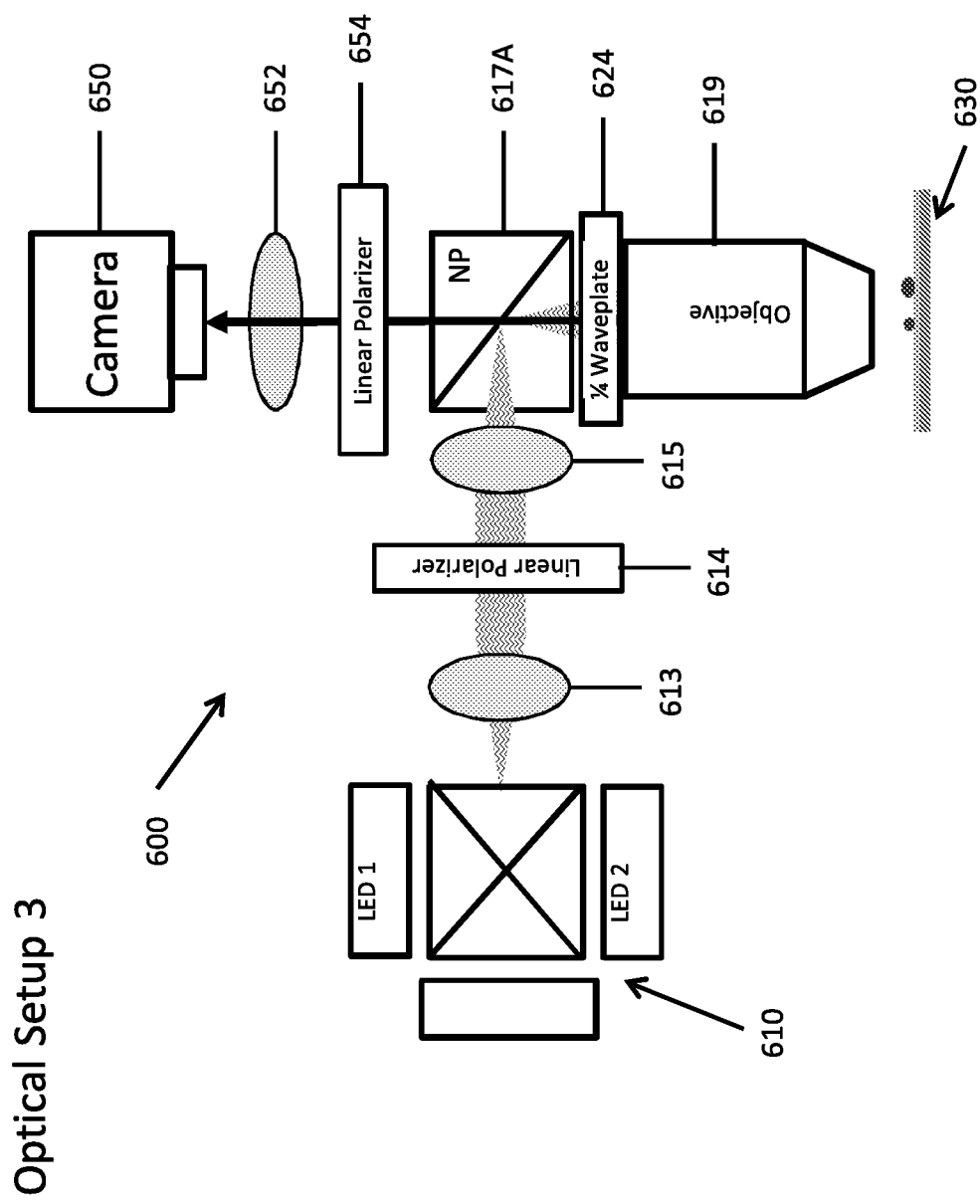
FIG. 6B shows a diagram of an imaging system according to an alternate embodiment of the invention.

FIG. 6B shows an IRIS polarization sensitive imaging system 600 according to some alternative embodiments of the invention. The IRIS polarization sensitive imaging system 600 shown in FIG. 6B is similar to the system shown in FIG. 6A, except that the polarizing beam splitter (617 in FIG. 6A) and quarter wave plate 624 are replaced with a non-polarizing beam splitter 617A and a pair of linear polarizers in the illumination path and the collection path.

Imaging system 600 can include an LED light source 610 for illuminating a target substrate 630. The illumination path can include focusing lenses 613 and 615, linear polarizer 614, a non-polarizing beam splitter 617A, and objective lens 619 that directs and focuses the polarized light on the target 630. The collection path can include objective lens 619, linear polarizer 654 and focusing lens 652 that focuses the light reflected from target 630 on the sensor of the imaging device 650. The linear polarizer 614 in the illumination path can be arranged orthogonally with respect to the linear polarizer 654 in the collection path. The target 630 can be mounted on an X, Y, and Z stage that enables the target 630 to be positioned with respect to the objective lens 619 for imaging and focusing.

Figure 6C:
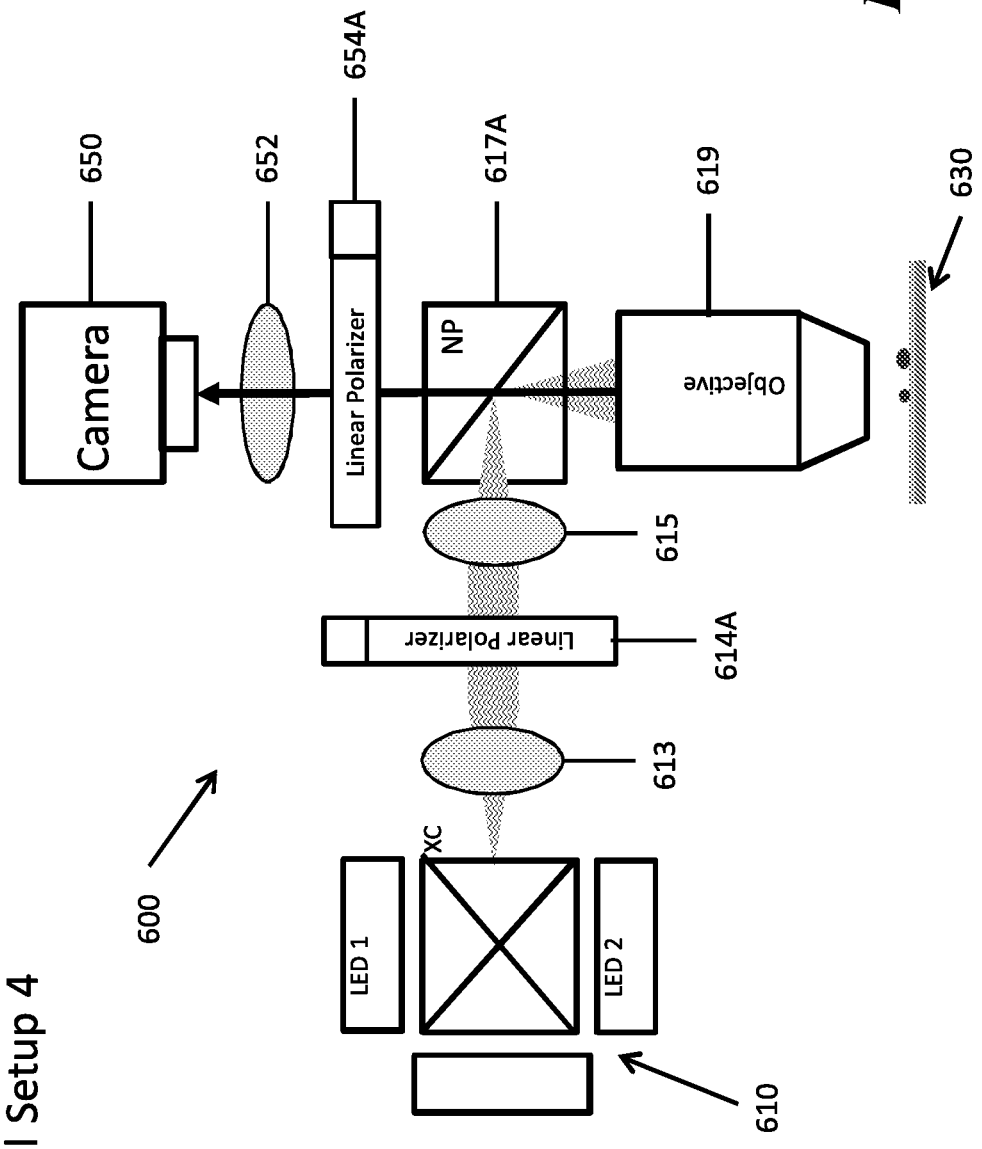
FIG. 6C shows a diagram of an imaging system according to an alternate embodiment of the invention.

FIG. 6C shows an IRIS polarization sensitive imaging system 600 according to some alternative embodiments of the invention. The IRIS polarization sensitive imaging system 600 shown in FIG. 6C is similar to the system shown in FIG. 6B, except that one or both of the linear polarizers 614A and 654A can be rotatable. One or both of the linear polarizers 614A and 654A can be mechanically rotatable using motors or electronically using a liquid crystal polarization rotator (Meadowlark Optics, Frederick, Colo.) or other solid state retarder. The motors and/or electronically controlled linear polarizers can be computer controlled according to a computer program stored in memory and executed by a processor of the computer (not shown). In this embodiment, images can be taken when the linear polarizers are in an orthogonal configuration such that the reflected light polarized by the linear polarizer 614 on the illumination path is blocked by the orthogonally oriented linear polarizer 654 on the collection path, but light scattered by objects or nanoparticles that result in a change in the polarization orientation of the scattered light will pass through to the imaging device 650. In accordance with some embodiments, images can be taken when the polarization of one or both of the linear polarizers is, for example, 10 degrees, 7.5 degrees, 5 degrees, 2.5 degrees, 1 degree, 0.5 degrees, 0.25 degrees, or any other amount offset from orthogonal in one or both directions. In accordance with some embodiments, additional images at greater or lesser offsets can be taken as well. Some or all of the images can be processed (e.g., by a computer or signal processor) to identify and count nanoparticles. For example, computer program can select the image having the highest contrast and then count the nanoparticles.

In accordance with some embodiments, the amount of rotation can be optimized for the substrate configuration, light wavelength and nanoparticle size. In some embodiments, the one or both polarizers can be rotated (e.g., manually or by a computer under program control) from the center or orthogonal position in one direction while the camera takes images and each succeeding image can be compared to the previous image to determine the position of maximum contrast or optimal filtering for a given configuration (e.g., manually or by a computer under program control), substrate configuration, light wavelength and nanoparticle size). For example, when previous image has a higher level of contrast than the current image, the position at which the previous image was taken can be selected as the position of maximum contrast and stored for a given substrate configuration, light wavelength and/or nanoparticle size. In accordance with some embodiments, the polarizer can be rotated incrementally (e.g., 0.5 or 1 degree increments), either manually or by a computer under program control, in one direction and, optionally, then in the other direction to maximum of deviation (e.g., 10 degrees, 9 degrees, 8 degrees, 7 degrees, 6 degrees, or 5 degrees) and an image taken at each position can be analyzed (e.g., manually or by a computer under program control) to determine a level of contrast and the position corresponding to the highest level of contrast can be selected (e.g., manually or by a computer under program control) as the maximum deviation for a given substrate, light wavelength and/or nanoparticle size.

Figure 7:
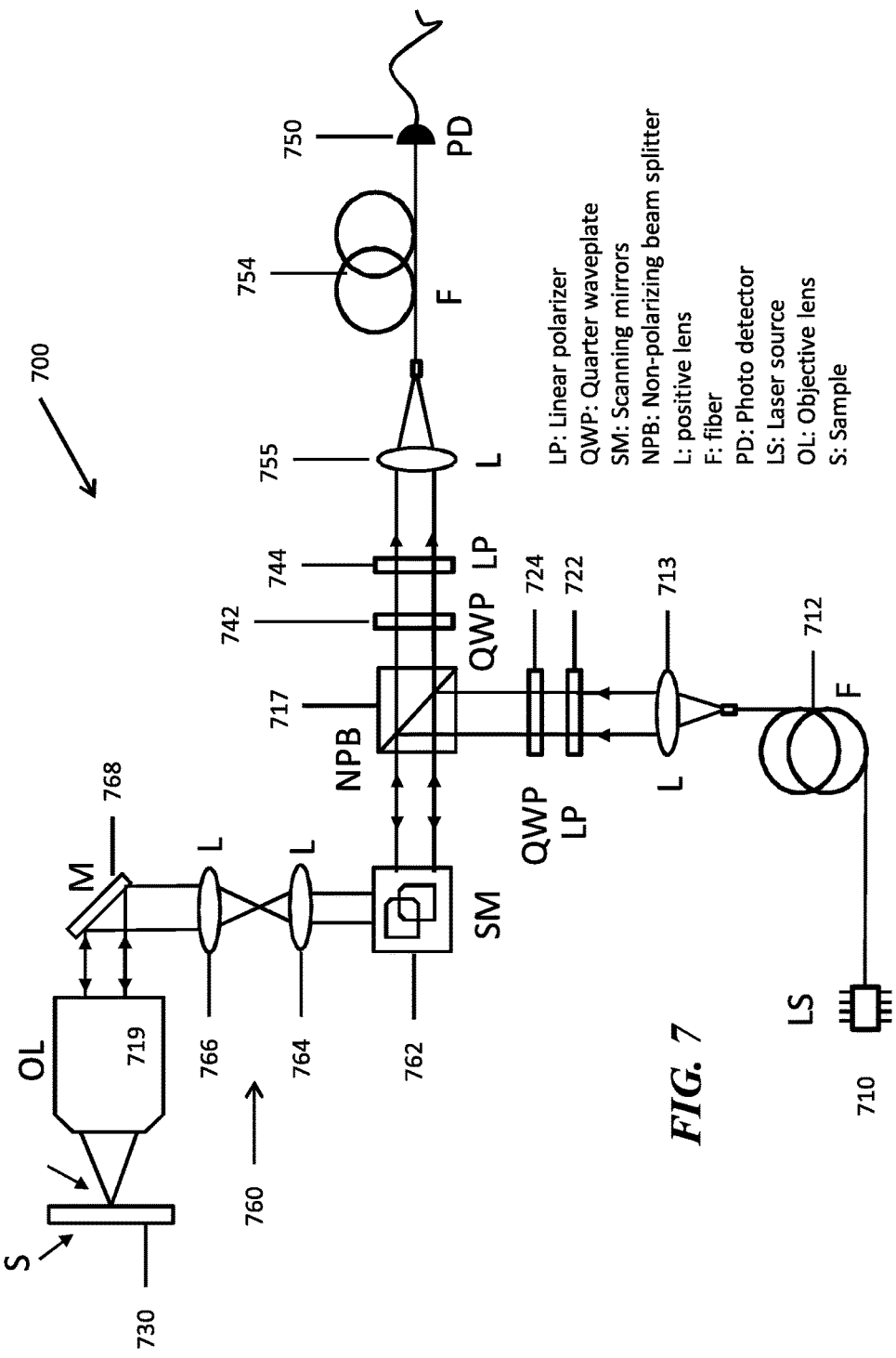
FIG. 7 shows a diagram of an imaging system according to a further embodiment of the invention.

FIG. 7 shows a diagrammatic view of a laser scanning microscope 700 according to some embodiments of the invention. This embodiment includes a LASER light source 710 that directs illumination light through an optical fiber 712 in the illumination path toward a target 730. The illumination path can include a focusing lens 714, a linear polarizer 722, a quarter wave plate 724, a non-polarizing beam splitter 717, a scanning mechanism 760, and an objective lens 719. The scanning mechanism 760 causes the laser light to scan over the surface of the target 730 and causes the light reflected by the target 730 to be directed toward the photo detector 750. The scanning mechanism 760 can include a one or more scanning mirrors 762, a first focusing lens 764, second focusing lens 766, and a mirror 768. The collection path includes the objective lens 719, the scanning mechanism 760, the beam splitter 717, a quarter waveplate 742, linear polarizer 744, focusing lens 752, optical fiber 742, and photo detector 750.

In operation, the illumination light takes the form of a LASER beam the produces a spot that is scanned over the surface of the target 730 using scanning mechanism 760. The reflected light on the collection path is uses the scanning mechanism 760 to direct the reflected signal to the photo detector 750 which measures the intensity of the reflection from an array of positions on the target surface. The measured intensity can be recorded by a recording device, such as a computer. The LASER light on the illumination path can be circularly polarized by the linear polarizer 722 and the quarter waveplate 724 and the reflected light on the collection path can be filtered by the quarter waveplate 742 and linear polarizer 744. The position of the LASER beam on the surface of the target 730 can be tracked by a controller or a computer system. The light intensity detected by the photo detector 750 can be associated with a position on the target 730 to construct an image of the target 730.

Figure 8:
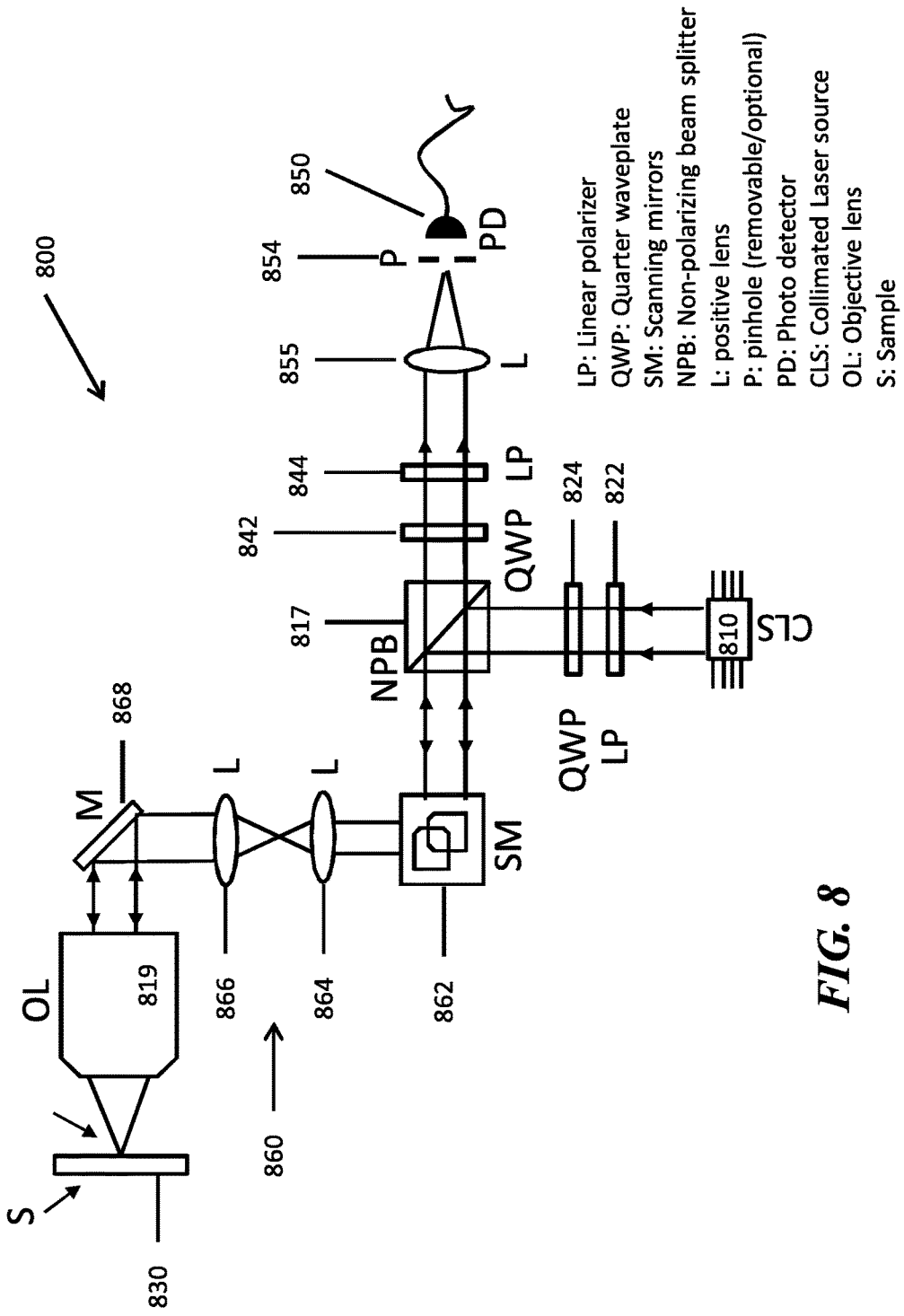
FIG. 8 shows a diagram of an imaging system according to a further embodiment of the invention.

FIG. 8 shows a diagrammatic view of a laser scanning microscope 800 according to some embodiments of the invention. This embodiment includes a collimated LASER light source 810 that directs illumination light along the illumination path toward a target 830. The illumination path can include a linear polarizer 822, a quarter wave plate 824, a non-polarizing beam splitter 817, a scanning mechanism 860, and an objective lens 819. The scanning mechanism 860 causes the laser light to scan over the surface of the target 830 and causes the light reflected by the target 830 to be directed toward the photo detector 850. The scanning mechanism 860 can include a one or more scanning mirrors 862, a first focusing lens 864, second focusing lens 866, and a mirror 868. The collection path includes the objective lens 819, the scanning mechanism 860, the beam splitter 817, a quarter waveplate 842, linear polarizer 844, focusing lens 852, optional pinhole filter 854, and photo detector 850. The optional pinhole filter 854 can be used to remove the unfocused light from the collection path.

In operation, the illumination light takes the form of a collimated LASER beam that produces a spot that is scanned over the surface of the target 830 using scanning mechanism 860. The reflected light on the collection path is uses the scanning mechanism 860 to direct the reflected signal to the photo detector 850 which measures the intensity of the reflection from an array of positions on the target surface. The measured intensity can be recorded by a recording device, such as a computer. The LASER light on the illumination path can be circularly polarized by the linear polarizer 822 and the quarter waveplate 824 and the reflected light on the collection path can be filtered by the quarter waveplate 842 and linear polarizer 844. The position of the LASER beam on the surface of the target 830 can be tracked by a controller or a computer system. The light intensity detected by the photo detector 850 can be associated with a position on the target 830 to construct an image of the target 830.

Figure 9:
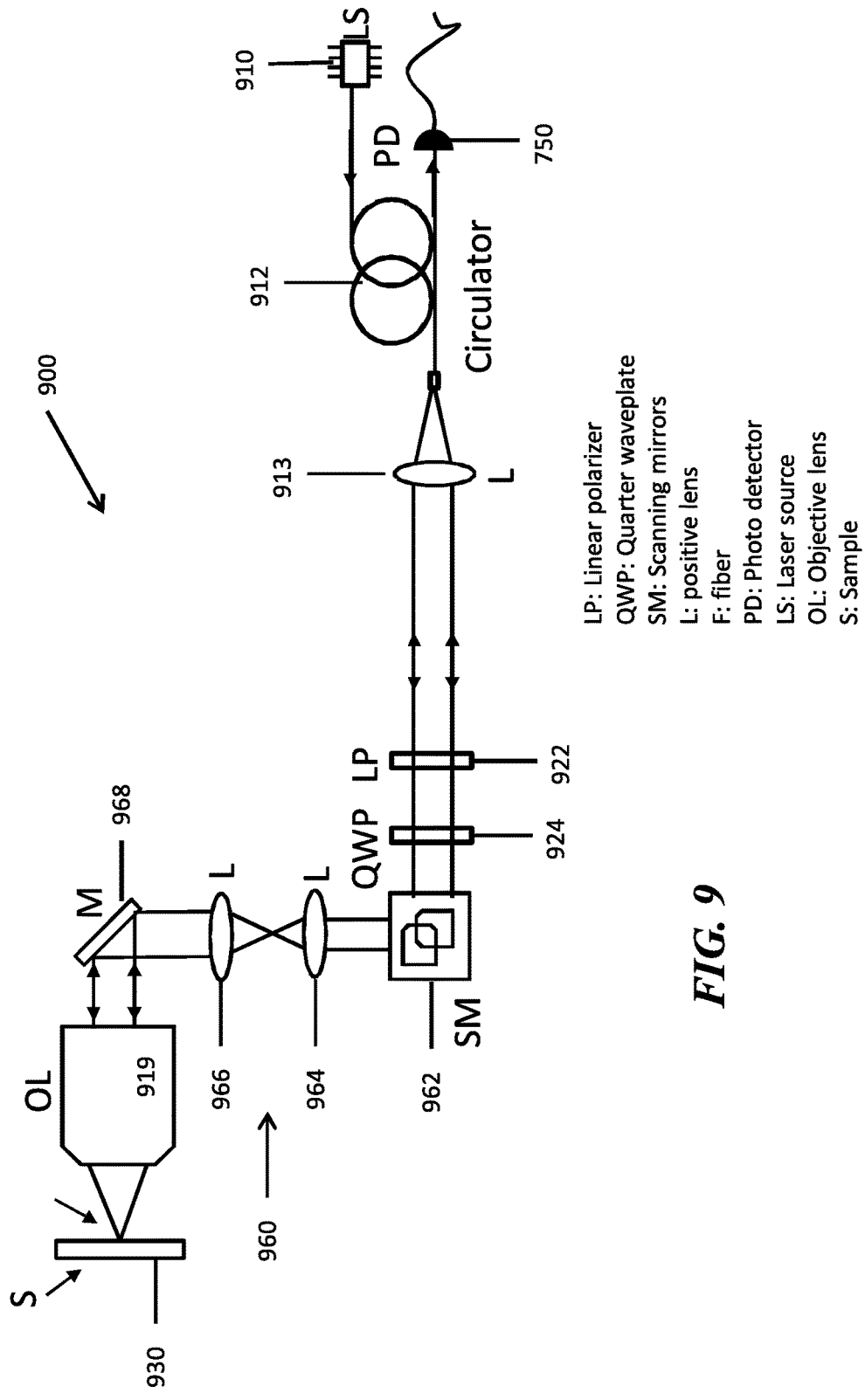
FIG. 9 shows a diagram of an imaging system according to a further embodiment of the invention.

FIG. 9 shows a diagrammatic view of a laser scanning microscope according to some embodiments of the invention. The embodiment shown in FIG. 9 is similar to FIG. 8, except the illumination path and the collection path follow a common path up to an optical circulator 912 that joins the illumination light from LASER source 910 onto the common path and separates the reflected light from common path for connection to the photo detector 950. This embodiment obviates the need for a beam splitter.

The embodiment shown in FIG. 9 includes a LASER light source 910 that directs illumination light along the illumination path toward a target 930. The illumination path can include an optical circulator 912, a linear polarizer 922, a quarter wave plate 924, a scanning mechanism 960, and an objective lens 919. The scanning mechanism 960 causes the laser light to scan over the surface of the target 930 and causes the light reflected by the target 930 to be directed toward the photo detector 950. The scanning mechanism 960 can include a one or more scanning mirrors 962, a first focusing lens 964, second focusing lens 966, and a mirror 968. The collection path includes the objective lens 919, the scanning mechanism 960, the quarter waveplate 924, the linear polarizer 922, the focusing lens 913, the optical circulator 912, and photo detector 950.

In operation, the illumination light takes the form of a LASER beam that produces a spot that is scanned over the surface of the target 930 using scanning mechanism 960. The reflected light on the collection path uses the scanning mechanism 960 to direct the reflected signal to the photo detector 950 which measures the intensity of the reflection from an array of positions on the target surface. The measured intensity can be recorded by a recording device, such as a computer. The LASER light on the illumination path can be circularly polarized by the linear polarizer 922 and the quarter waveplate 924 and the reflected light on the collection path can be filtered by the same quarter waveplate 924 and linear polarizer 922. The position of the LASER beam on the surface of the target 930 can be tracked by a controller or a computer system. The light intensity detected by the photo detector 950 can be associated with a position on the target 930 to construct an image of the target 930.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

Further, while the description above refers to the invention, the description may include more than one invention.

What is claimed is:

1. An interferometric reflectance imaging system comprising:

a target including a substrate having a first reflecting surface and a transparent layer on the first reflecting surface forming a second reflective surface separated from the first reflecting surface by a thickness of the transparent layer;

a light source configured to produce illumination light along an illumination path toward the target, the illumination light being polarized according to a first polarization configuration;

wherein the first reflecting surface and the second reflecting surface of the target is positioned to receive the illumination light and reflect the illumination light along a collection path toward an imaging sensor and result in signal interference in the reflected illumination light; and a filter positioned in the collection path to filter light polarized according to the first polarization configuration whereby substantially all of the reflected illumination light reflected by the first reflecting surface and the second reflecting surface is not received by the imaging sensor.

2. The interferometric reflectance imaging system according to claim 1 wherein the illumination light is circularly polarized and the filter is configured to filter the circularly polarized light.

3. The interferometric reflectance imaging system according to claim 1 further comprising a linear polarizer and a quarter waveplate positioned in the illumination path between the light source and the target.

4. The interferometric reflectance imaging system according to claim 1 further comprising a quarter waveplate and a linear polarizer positioned in the collection path between the target and the imaging sensor.

5. The interferometric reflectance imaging system according to claim 4 wherein the linear polarizer can be adjusted to change an angle of linear polarization of the linear polarizer.

6. The interferometric reflectance imaging system according to claim 1 wherein the illumination light is linearly polarized according to a first angle and the filter is configured to filter light polarized according to the first angle.

7. The interferometric reflectance imaging system according to claim 1 further comprising a linear polarizer positioned in the illumination path between the light source and the target.

8. The interferometric reflectance imaging system according to claim 1 further comprising a linear polarizer positioned in the illumination path between the light source and the target having an adjustable angle of polarization.

9. The interferometric reflectance imaging system according to claim 1 further comprising a linear polarizer positioned in the collection path between the target and the imaging sensor.

10. The interferometric reflectance imaging system according to claim 1 further comprising a linear polarizer positioned in the collection path between the target and the imaging sensor having an adjustable angle of polarization.

11. The interferometric reflectance imaging system according to claim 1 wherein the light source includes at least one LED.

12. The interferometric reflectance imaging system according to claim 1 wherein the light source includes a LASER light source.

13. The interferometric reflectance imaging system according to claim 1 further comprising a linearly polarizing beam splitter positioned between the light source and the target.

14. The interferometric reflectance imaging system according to claim 13 further comprising a quarter wave plate positioned between the linearly polarizing beam splitter and the target.

15. The interferometric reflectance imaging system according to claim 1 wherein the target includes at least one nanorod on a surface of the target.

16. The interferometric reflectance imaging system according to claim 1 wherein the second reflecting surface includes at least one nanorod arranged on the surface.

17. The interferometric reflectance imaging system according to claim 16 wherein the at least one nanorod is not greater than 40 nm long and not greater than 10 nm wide.

18. The interferometric reflectance imaging system according to claim 1 wherein the second reflecting surface includes an array of nanorods arranged on the surface.

19. The interferometric reflectance imaging system according to claim 18 wherein at least one nanorod in the array is not greater than 40 nm long and not greater than 10 nm wide.

20. The interferometric reflectance imaging system according to claim 1 wherein the imaging device includes a camera having a CCD imaging sensor.

21. An imaging system comprising:
a target including a nanoparticle attached to a substrate, the substrate having a first reflecting surface and a transparent layer on the first reflecting surface forming a second reflective surface separated from the first reflecting surface by a thickness of the transparent layer;
a light source configured to produce illumination light along an illumination path toward the target, the illumination light being polarized according to a first polarization configuration;
wherein the first reflecting surface and the second reflecting surface of the target is positioned to receive the illumination light and reflect the illumination light along a collection path toward an imaging sensor and result in signal interference in the reflected illumination light; and
a filter positioned in the collection path to filter light polarized according to the first polarization configuration whereby illumination light that has interacted with the nanoparticle is received by the imaging sensor and substantially all of the reflected illumination light reflected by the first reflecting surface and the second reflecting surface is not received by the imaging sensor.

* * * * *